United States Patent [19]

Roller et al.

[11] 4,018,967
[45] Apr. 19, 1977

[54] MAGNETIC RECORDING TAPE

[75] Inventors: Hermann Roller, Ludwigshafen; Werner Senkpiel, Laudenbach; Gerd Wunsch, Speyer; Job-Werner Hartmann, Ludwigshafen; Friedrich Fuchs, Kirchheim; Joachim Hack, Ludwigshafen; Volker Kiener, Ludwigshafen; Herbert Motz, Ludwigshafen; Werner Ostertag, Willstaett, all of Germany

[73] Assignee: BASF Aktiengesellschaft, Ludwigshafen, Germany

[22] Filed: Sept. 19, 1974

[21] Appl. No.: 507,466

[30] Foreign Application Priority Data

Oct. 5, 1973 Germany .................. 2350062

[52] U.S. Cl. ................ 428/425; 252/62.54; 428/900
[51] Int. Cl.$^2$ ........................ H01F 10/02
[58] Field of Search ............ 117/235–240, 117/161 UA; 252/62.54; 427/127–132, 47, 48; 428/539, 425, 900

[56] References Cited

UNITED STATES PATENTS

| | | | |
|---|---|---|---|
| 3,492,235 | 1/1970 | Matsumoto et al. | 117/235 X |
| 3,625,760 | 12/1971 | Slovinsky | 117/235 |
| 3,692,884 | 9/1972 | Gaskell | 117/235 X |
| 3,704,152 | 11/1972 | Hartmann et al. | 117/237 X |
| 3,719,525 | 3/1973 | Patel et al. | 117/237 |
| 3,778,308 | 12/1973 | Roller et al. | 117/237 X |
| 3,793,074 | 2/1974 | Frankenthal et al. | 117/235 |

Primary Examiner—Bernard D. Pianalto
Attorney, Agent, or Firm—Johnston, Keil, Thompson & Shurtleff

[57] ABSTRACT

Magnetic recording tape especially suitable for use as video tape and computer tape, comprising a base carrying a magnetic coating which consists essentially of a dispersion of a finely divided magnetic pigment and at least one lubricant in an organic binder. The lubricant is a compound of the formula

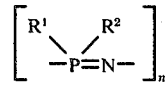

in which $n$ is an integer of from 3 to 8 and $R^1$ and $R^2$ are an alkoxy or aralkoxy radical or conjointly are an alkyldioxy radical of 3 to 18 carbon atoms. A magnetic recording tape prepared with a high proportion of such a lubricant is distinguished by high abrasion resistance coupled with a minimum transfer of material to the magnetic heads even under fluctuating climatic conditions.

6 Claims, No Drawings

MAGNETIC RECORDING TAPE

This application discloses and claims subject matter described in German Pat. No. P 23 50 062.1, filed Oct. 5, 1973, which is incorporated herein by reference.

The invention is concerned with coated magnetic recording media and in particular with video tapes and computer tapes which have advantageous self-lubricating properties.

Magnetic tapes for use as video tapes and computer tapes must have high abrasion resistance coupled with excellent frequency characteristics and high recording and playback sensitivity. For example, in television recording equipment, the relative velocity between the magnetic head and the magnetic tape in contact with it is in excess of 20 m/sec. When using a computer tape, the magnetic tape is particularly subjected to wear as a result of the frequent changes in direction of travel of the tapes before the head. The abrasion resistance and life of the magnetic coatings of such tapes are of particular importance.

It is known that coated magnetic recording media of improved abrasion resistance can be manufactured by adding solid or liquid lubricants, such as graphite, molybdenum disulfide, stearic acid, oleic acid, fatty acid esters, petroleum jelly or mineral oil to the magnetic coatings.

German Pat. No. 1,005,754 and U.S. Pat. No. 3,003,965 have disclosed the addition of acid phosphorus compounds and German Pat. No. 1,669,602 has disclosed the addition of a divalent or trivalent salt of an oxy-acid derived from phosphorus and having organic groups of at least 8 carbon atoms. A disadvantage of the use of the acid phosphorus compounds is that they impair somewhat the magnetic properties of the tapes containing gamma-iron-(III) oxide. The other conventional lubricant additives also do not provide the properties required for industrial applications.

Essential factors in high sensitivity and good characteristics for recording high data densities are the choice of the magnetic pigment, the packing density of the magnetic material in the magnetic coating, as smooth a surface of the magnetic coating as possible, and a tape which is as flexible and supple as possible under all climatic conditions. It was the object of the present invention to provide a magnetic tape improved in this respect, which substantially has the required properties, exhibits uniform internal lubrication of the magnetic coating whilst at the same time the magnetic tapes remain plane under all climatic conditions, and is particularly suitable for use as a magnetic recording medium of long life, high sensitivity and good frequency response for video and computer recordings.

We have found that coated magnetic recording media comprising a base carrying a magnetic coating, which essentially consists of a dispersion of a finely divided magnetic pigment and at least one lubricant in a binder, substantially exhibit the desired properties if the lubricant they contain is a compound of the formula (I):

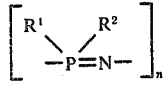

wherein $n$ is an integer of from 3 to 8, $R^1$ and $R^2$ are identical or different, optionally halogen-substituted alkoxy or aralkoxy of 3 to 18 carbon atoms or $R^1$ and $R^2$ conjointly are a $-O-R^3-O-$ radical in which $R^3$ is a divalent aliphatic radical of 3 to 18 carbon atoms.

The compounds of the formula (I) can be manufactured by conventional methods, for example by reacting phosphonitrile chlorides with alcohols, above all monoalcohols or glycols. Thus, for example, reaction of the cyclic trimeric phosphonitrile chloride with propanol gives hexapropoxy-triphosphotrinitride (formula II, R = propyl). The trimers of the formulae (II) and (III)

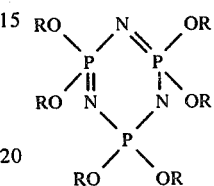

(II) R = alkyl or aralkyl of 3 to 18 carbon atoms

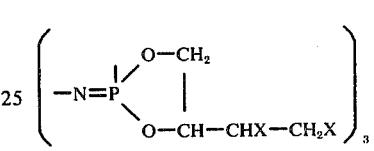

(III) X = Cl or Br are particularly suitable; the compounds of the formula (III) can be manufactured by, for example, reaction of cyclic phosphonitrile chlorides with vinylglycol followed by halogenation of the vinyl side chains. Mixtures of compounds of the formula (I) can also be used and in fact frequently result from the manufacturing process, since the phosphonitrile chlorides themselves are frequently mixtures of compounds of different degrees of polymerization.

Of course it is possible and in some cases advantageous, to use mixtures of the lubricants of the formula (I) with other conventional slip agents or lubricants, such as, in particular, alkyl esters of fatty acids or aliphatic dicarboxylic acids, wherein the esters preferably are of at least 16 carbon atoms, or polysiloxanes. It is surprising that a distinct improvement in the resulting magnetic recording medium is achieved with such mixtures even if only about 20 percent by weight of the total lubricant consists of compounds of the formula (I). In general, the content of compounds of the formula (I) is from about 20 to 100 percent by weight of the total amount of lubricants employed.

The conventional organic, mostly polymeric, binders such as vinyl chloride polymers, acrylate polymers, polyvinyl acetals, such as polyvinyl formal or polyvinyl butyral, higher-molecular epoxide resins, polyesters, polycarbonates, polyurethanes and mixtures of these and similar binders can be used as binders for the magnetic recording media according to the invention. Polyester-polyurethanes and polyether-polyurethanes which are soluble in volatile organic solvents have proved very suitable, and amongst these, particularly, polyurethanes which are obtained from a linear aliphatic polyester or polyether and a polyisocyanate, are elastomeric and practically free from isocyanate groups, and are in some cases commercially available (compare Saunders-Frisch, Polyurethanes, Chemistry and Technology, Part II, Chapter IX, New York, 1964 and the literature quoted there, and also U.S. Pat. No. 2,899,411 and German Pat. No. 1,106,959). Elastomeric linear polyester-urethanes which can be obtained by reaction of hydroxyl-containing linear polyesters, obtained from an aliphatic diol of 2 to 6 carbon atoms and an aliphatic dicarboxylic acid of 2 to 12 carbon atoms and optionally an aliphatic hydroxycarboxylic acid or its lactone of 3 to 12 carbon atoms, and a diisocyanate, under conditions such that all isocyanate groups can react with a hydroxyl group, have proved particularly suitable.

Amongst the above, the elastic thermoplastic reaction products of hydroxyl-containing thermoplastic polyesters of adipic acid and 1,4-butanediol and/or ethylene glycol with diisocyanates such as, in particular, 4,4'-diisocyanatodiphenylmethane, 4,4'-diisocyanatodiphenylpropane, 4,4'-diisocyanatodicyclohexylmethane, 4,4'-diisocyanatodicyclohexylpropane, 1,5-naphthylenediisocyanate or toluylenediisocyanate are preferred. The preferred polyurethanes contain no significant amounts of reactive isocyanate groups, and have good extensibility (elongation at break approximately from 400 to 700%) and a number-average molecular weight of approximately from 10,000 to 60,000. Their Shore A hardness is approximately from 60 to 100. The preferred polyurethanes are soluble in organic solvents such as tetrahydrofuran, tetrahydrofuran-toluene mixtures, dioxane, cyclohexanone and dimethylformamide and some of them also in ketones, such as methyl ethyl ketone or acetone.

Binder mixtures in which the polyurethanes mentioned have been combined with other binders, have also shown favorable characteristics.

In general, the proportion of the polyurethanes is at least 30 and preferably from 50 to 95 percent by weight of the total amount of binder. Amongst the binders used in combinations, vinyl chloride copolymers and vinylidene chloride copolymers which contain at least 70 percent by weight of vinyl chloride units or vinylidene chloride units should be mentioned particularly. The comonomer units can in particular be vinyl esters, such as vinyl acetate, vinyl alcohol, esters of olefinically unsaturated carboxylic acids of 3 to 5 carbon atoms (in the acid part) and of 1 to 17 carbon atoms in the alcohol part of the ester, for example diethyl maleate, n-butyl acrylate or 2-ethylhexyl methacrylate, and also the said acids themselves. Further binder components which have proved very suitable are epoxide resin binders and amongst these particularly the high-molecular weight condensates of bisphenol A with epichlorohydrin, which are commercially available.

The conventional magnetic pigments can be used though the final properties of the magnetic coating also depend on the magnetic pigment used. Examples of the magnetic pigments are gamma-iron-(III) oxide, finely divided magnetite, ferromagnetic chromium dioxide, cobalt-modified γ-iron oxide and ferromagnetic metals and metal alloy pigments, such as alloys of iron, cobalt and nickel or of iron and cobalt (for example manufactured by the method in German Pat. No. 1,247,027). The preferred magnetic pigment is acicular gamma-iron-(III) oxide. The particle size is in general from 0.2 to 2$\mu$, and the range from 0.3 to 0.8$\mu$ is preferred.

The ratio or magnetic pigment to binder in the recording media according to the invention is in general from 1 to 10 and especially from 4 to 6 parts by weight of magnetic pigment per part by weight of the binder mixture.

The non-magnetic and non-magnetizable base materials used are the conventional materials, in particular films of linear polyesters, such as polyethylene terephthalate, in general in gauges of from 4 to 200$\mu$ and especially of from 10 to 36$\mu$.

The magnetic coatings can be produced by conventional methods. A suitble method is to prepare the dispersion from the magnetic pigment and a solution of the binder, dispersing agents, the lubricant and optionally other additives in a dispersing apparatus, for example a tube mill or a stirred ball mill, to filter the dispersion and to apply it to the non-magnetizable base material using a conventional coating machine, for example a knife coater. As a rule, the liquid coating mixture is subjected to magnetic orientation before it is dried on the base material; drying is suitably carried out for from 2 to 5 minutes at temperatures of from 50° to 90° C. The magnetic coatings can be smoothed and densified on conventional machinery by passing them between heated and polished rollers, if necessary using pressure and temperatures of from 50° to 100° C, preferably from 60° to 80° C. The thickness of the magnetic coatings is in general from 3 to 20$\mu$, preferably from 8 to 15$\mu$.

The coated magnetic recording media according to the invention are distinguished by high abrasion resistance coupled with only little transfer of material to the magnetic heads, high stability under changing climatic conditions and non-cupping of the tapes under adverse climatic conditions, and at the same time have high sensitivity in recording and playback.

The parts and percentages mentioned in the Examples which follow, and in the comparative experiment, are by weight unless stated otherwise. Parts by volume bear the same relation to parts as the liter to the kilogram.

EXPERIMENT A (COMPARATIVE EXPERIMENT)

8,000 parts of 6 mm steel balls are introduced into a cylindrical steel mill of capacity 6,000 parts by volume and the following mixture is added: 700 parts of rod-shaped finely particulate gammairon-(III) oxide, 10.5 parts of soya lecithin, 4.2 parts of dioctyl azelate, 2.1 parts of polydimethylsiloxane, 250 parts of tetrahydrofuran, 250 parts of dioxane, 42 parts of carbon black and 1,360 parts of a 15% strength binder solution prepared by dissolving 192 parts of an elastomeric, thermoplastic polyester-urethane (prepared according to German Pat. No. 1,106,959 from adipic acid, 1,4-butanediol and 4,4'-diisocyanatodiphenylmethane) and 48 parts of a commercially available high molecular weight epoxy resin, obtained from bisphenol A and epichlorohydrin and having an expoxide equivalent weight of approx. 10,000, in 1,360 parts of a mixture of equal parts of tetrahydrofuran and dioxane. The dispersing treatment is carried out for 92 hours and the dispersion is then filtered under pressure through a paper filter. The dispersion is used to coat a 36$\mu$polyethylene terephthalate film, the magnetic pigments being oriented by means of a permanent magnet. After drying, the resulting magnetic coating is 10$\mu$ thick. The magnetic films are cut into ½ inch wide tapes, which are tested and give the following result:

| | |
|---|---|
| Coercive force (oersted) | 297 (23.6 kA/m) |
| Orientation ratio (Ratio of residual induction in the direction of tape travel to residual | 1.7 |

| | |
|---|---|
| induction in the crosswise direction) Electrical surface resistance of the magnetic coating (M ohm per square) | 69 |

EXAMPLE 1

A magnetic tape is produced exactly as described under experiment A, but in addition to the materials mentioned, 4.8 parts of hexapropoxytriphosphotrinitride (formula II, R = propyl) are charged into the steel mill. Tests on the tape, which in other respects was produced exactly as before, gave the following results:

| | |
|---|---|
| Coercive force (oersted) | 307 (24.4 kA/m) |
| Orientation ratio | 1.9 |
| Electrical surface resistance of the magnetic coating (M ohm per square) | 29 |

Comparative test of the tapes, produced according to experiment A and according to Example 1, on a computer tape deck:

11 cm long pieces from each of the two types of tape were subjected to 50,000 reversals on an IBM 2401 computer tape deck. The increase in drop-out, the state of the signal level envelope, the tape surfaces and the condition of the magnetic head system were assessed.

For both types of tape, the drop-out rate and the signal level curves were approximately the same. The surface of the tape produced according to experiment A showed clearly visible signs of wear whilst the surface of the tape produced according to Example 1 appeared practically unchanged. When testing the tape from experiment A, brown material deposited on the magnetic heads was detectable at the end of the test, but not in the case of the test of the tape from Example 1.

EXAMPLE 2

The procedure followed is as in Example 1 but intead of 4.8 parts of hexapropoxytriphosphotrinitride 5.8 parts of the compound of the formula III, wherein X is bromine, are added. Tests on the tape, which in other respects was produced exactly as before, gave the following result:

| | |
|---|---|
| Coercive force (oersted) | 305 (24.3 kA/m) |
| Orientation ratio | 1.95 |
| Electrical surface resistance of the magnetic coating (M ohm per square) | 25 |

A comparative test on a computer tape deck — as described in Example 1 — showed the same advantageous properties as in the case of the tape from Example 1.

EXAMPLE 3

The procedure followed is as in Example 1, but instead of the mixture of 4.2 parts of dioctyl azelate, 2.1 parts of polydimethylsiloxane and 4.8 parts of hexapropoxytriphosphotrinitride, 11.1 parts of the latter material are added. Tests on the tape, which in other respects was produced exactly as before, gave the following result:

| | |
|---|---|
| Coercive force (oersted) | 307 (24.4 kA/m) |
| Orientation ratio | 2.0 |
| Electrical surface resistance of the magnetic coating (M ohm per square) | 15 |

In a comparative test on a computer tape deck, carried out as indicated above, the drop-out rate and the signal level curve of the tape were again approximately the same as for the tape produced according to comparative experiment A. The surface of the tape produced according to Example 3 was practically unchanged at the end of the experiment and there were no deposits on the magnetic head. The test was then repeated with the same piece of magnetic tape produced according to Example 3, and the same result was obtained.

We claim:
1. In a magnetic recording tape of the type comprising
   1. a base; and
   2. a magnetic coating carried on said base, said coating consisting essentially of a dispersion of a finely divided magnetic pigment and at least one lubricant in an organic binder, the improvement which comprises: using as a lubricant in said coating at least one compound of the formula (I)

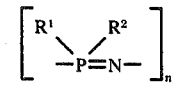

in which $n$ is an integer of from 3 to 8, $R^1$ and $R^2$ are identical or different and are alkoxy or aralkoxy of 3 to 18 carbon atoms, alkoxy and aralkoxy substituted with bromine or chlorine or $R^1$ and $R^2$ conjointly are a —O—$R^3$—O— radical in which $R^3$ is a divalent aliphatic radical of 3 to 18 carbon atoms, wherein said compound of the Formula I constitutes from about 20 to about 100% by weight of the lubricant in the coating.

2. A magnetic recording tape as set forth in claim 1 wherein the lubricant present is a compound of the formula

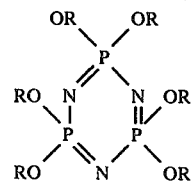

(II)

in which R is alkyl or aralkyl of 2 to 18 carbon atoms.

3. A magnetic recording tape as set forth in claim 1 wherein the lubricant present is a compound of the formula (III)

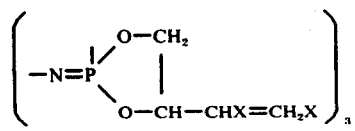 (III)
in which X is chlorine or bromine.
4. A magnetic recording tape as set forth in claim 1 wherein at least 30 percent by weight of the binder employed is an elastomeric polyurethane binder.
5. A magnetic recording tape as set forth in claim 2 wherein R is an n-propyl group.
6. A magnetic recording tape as set forth in claim 3 wherein R is bromine.
* * * * *